(12) United States Patent
Vimegnon et al.

(10) Patent No.: US 10,517,513 B2
(45) Date of Patent: Dec. 31, 2019

(54) HAND FUNCTION DIAGNOSTIC AND THERAPEUTIC SYSTEM

(71) Applicants: Yves Vimegnon, Portland, OR (US); Gregory Landry, Portland, OR (US)

(72) Inventors: Yves Vimegnon, Portland, OR (US); Gregory Landry, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 775 days.

(21) Appl. No.: 14/927,944

(22) Filed: Oct. 30, 2015

(65) Prior Publication Data

US 2016/0120446 A1 May 5, 2016

Related U.S. Application Data

(60) Provisional application No. 62/073,830, filed on Oct. 31, 2014.

(51) Int. Cl.
*A61B 5/00* (2006.01)
*A61B 5/11* (2006.01)

(52) U.S. Cl.
CPC .......... *A61B 5/1125* (2013.01); *A61B 5/1126* (2013.01); *A61B 5/70* (2013.01); *A61B 2505/09* (2013.01)

(58) Field of Classification Search
CPC ....... A61B 5/11; A61B 5/1125; A61B 5/1126; A61B 5/70; A61B 5/742; A61B 2505/09; A61B 2562/033
See application file for complete search history.

(56) References Cited

U.S. PATENT DOCUMENTS

| 5,125,270 | A  | * | 6/1992  | Kovacevic | A61B 5/225 600/587 |
| 6,526,669 | B2 | * | 3/2003  | Nagata    | A61B 5/1125 33/503 |
| 6,827,549 | B1 | * | 12/2004 | Horng     | F04D 29/582 415/193 |
| 8,291,762 | B2 | * | 10/2012 | Akins     | G09B 19/003 73/379.02 |
| 8,827,718 | B2 | * | 9/2014  | Chiu      | A61B 5/1071 434/258 |
| 9,345,424 | B2 | * | 5/2016  | Wang      | A61B 5/103 |

* cited by examiner

*Primary Examiner* — Max F Hindenburg (57) ABSTRACT

Systems, devices and methods for quantitatively assessing hand function strength and range of motion via various instrumentations are disclosed. In one example embodiment, a hand function diagnostic and therapeutic system includes distal and proximal finger flexion measurement apparatuses used to automate quantitative assessment of hand function based on a combination of strength, range of motion, and time performance metrics.

15 Claims, 4 Drawing Sheets

HAND FUNCTION DIAGNOSTIC AND THERAPEUTIC SYSTEM

ACKNOWLEDGMENT OF GOVERNMENT SUPPORT

This invention was made with government support under HL080232 awarded by the National Institutes of Health. The government has certain rights in this invention.

FIELD

The present disclosure relates to the field of hand function assessment and rehabilitation.

BACKGROUND

Activities of daily living (ADL) have been suggested for the evaluation of hand function (Sollerman, C., & Sperling, L. (1978). Evaluation of Activities of Daily Living Function—Especially Hand Function. *Scandinavian Journal of Rehabilitative Medicine. Vol.* 6, 139-43, which is hereby incorporated by reference). In particular the Sollerman test has been suggested for patients undergoing long term haemodialysis (Limaye, V., Frankham, A., Disney, A., & Pile, K. (2001). Evaluation of Hand Function in Patients Undergoing Long Term Haemodialysis. *Annals of the Rheumatic Diseases. Vol.* 60, *Part* 3, 278-80, which is hereby incorporated by reference). However, clinical assessments like Sollerman require subjective ratings, which are time consuming and difficult to standardize.

The ability to objectively and effectively assess hand function is of great importance for clinicians in many medical and surgical specialties. Various measurement tools are subsequently used in research studies and routine practice. However, none is specifically built for the evaluation of dynamic hand function events such as those required in activities of daily living (ADL) like eating, opening a jar, closing a zipper, etc. Vascular Surgeons create access to dialysis for chronic kidney disease patients in their arms. This has been preferentially done in the non-dominant arms, partially due to concerns about adverse effects of the surgery on hand function in ADL. The available tools to evaluate hand function after surgery are unfortunately limited and inadequate for comprehensive measurements.

Patients undergoing kidney dialysis often suffer loss of hand function in the arm of access. Current metrics for assessing this loss are time consuming even for a skilled administrator. Furthermore, the impact on activities of daily living (i.e. opening or closing a jar, buttoning or zipping clothing) is poorly reflected in the assessment score. Vascular surgeons usually choose the non-dominant arm for an access site. However, the non-dominant arm is often not the best anatomical choice In one example study, out of 23 end-stage renal patients identified with finger gangrene, 12 (52%) necessitated repeat finger amputations, and 14 (61%) developed bilateral finger gangrene. Over 1,000,000 U.S. workers receive treatment in emergency departments for acute hand injuries annually. Surgery for Carpal Tunnel Syndrome (CTS) has been reported as the second most common type of surgery, with more than 230,000 procedures performed every year. Up to 30% of all CTS patients require unlimited medical care. Apart from finger gangrene in ESRD patients with AVF, acute hand injuries, and CTS, various neurological and rheumatological conditions also account for hand impairment or disability.

SUMMARY

The present disclosure is directed to systems, devices and methods used to quantitatively assess hand function strength and range of motion via various instrumentations. In one example embodiment, a hand function apparatus is described that may be used to automate quantitative assessment of hand function based on a combination of strength, range of motion, and time performance metrics is disclosed. Embodiments described herein may utilize digital transducers to measure hand functions associated with activities of daily living using instrumentation or measurement apparatuses to obtain measurements and provide tasks such as composite finger flexion, e.g., assessment of proximal and distal finger flexion using optical rotary encoders; vise grip, e.g., assessment of Jamar grip force using a load cell; jar/thermos grip, e.g., assessment of spherical Volar grip torque using a load cell; coin Pinch, e.g., assessment of pinch force using a load cell; key lock, e.g., assessment of pinch range of motion and torque using an optical rotary encoder and load cell; and door handle, e.g., assessment of transverse Volar grip range of motion and torque using an optical rotary encoder and load cell.

In embodiments, the various measurement apparatuses described herein may be used to perform measurements, e.g., 22 measurements, on both right and left hands for longitudinal assessment of hand function. The various measurement apparatuses described herein may include various sensors, e.g., isometric transducers, to detect and quantify various hand motions. For example, the strength generated by the isometric transducers may be measured and recorded digitally with electronic transmission to a main electronic board for data capture, storage and readout. A graphical user interface, e.g., an LCD display, may be included to provide instructions and/or visualizations of the test assessments generated from processed sensor readings.

Embodiments described herein may be used to measure various types of hand function including grip strength, rotational strength, range of motion and others using a single device. Such a device may be modular and portable and may be used to test different functional tasks of a user's hands. The results of the tests may be electronically recorded, for example. Embodiments described herein may incorporate a plurality of typical hand functions used in dialing living.

Embodiments described herein may be used to automate and objectify assessment of hand function based on the combination of strength, range of motion and time performance metrics and to seamlessly store and present hand function data. Embodiments described herein may be used in a variety of applications to monitor and track a patient's hand function in order to identify degradation in hand function at an early state so that appropriate treatment can be initiated. Clinicians can greatly benefit from such a system intended to integrate qualitative and quantitative data for optimal clinical decision making.

Embodiments described herein provide a hand function assessment system that may efficiently and accurately indicate the impact of dialysis on activities of daily living, for example. Armed with an improved assessment, vascular surgeons may have more freedom in their choice of access site.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the

DETAILED DESCRIPTION

The following detailed description is directed apparatuses, systems, and methods for automated quantitative assessment of hand function. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents. Various operations may be described as multiple discrete operations in turn, in a manner that may be helpful in understanding embodiments; however, the order of description should not be construed to imply that these operations are order dependent.

The inventors herein have studied hand function in dialysis patients and assessed the relationship of arteriovenous fistula (AVF) to finger gangrene in end-stage renal disease (ESRD). Finger gangrene was not found to be primarily due to dialysis access because of the prevalent comorbidities in the ESRD patients. However, repeat finger amputations were unavoidable in many of the cases, indicating that early detection of hand function impairment might be helpful. Therapeutic plans to prevent further complications and subsequent amputations were devised as a result. In order to achieve this goal, a health information and technology system was developed, which stands to also improve the quality of care of patients with other hand conditions across several medical and surgical specialties. The burden of hand dysfunction is a common and significant impediment to the quality of life of many patients, as the use of hand is an important body function.

The inventors herein have recognized that the Jamal hand dynamometer and pinch meter, the existing gold standard measurement devices, do not have seamless data capture, storage, and presentation, accessible from the point of care. Moreover, they do not measure activities of daily living (ADL) relevant to patient-centered care and quality of life. Accordingly, systems, devices and methods used to quantitatively assess hand function strength and range of motion via various instrumentations which at least partially overcome these issues are provided herein.

In embodiments, a hand function task box or apparatus may be used to automate quantitative assessment of hand function based on a combination of strength, range of motion, and time performance metrics. In embodiments, digital transducers may be used to measure hand functions most closely associated with activities of daily living using instrumentation to provide various tasks. Examples of such tasks that may be included in the system include the following:

1. Composite Finger Flexion, e.g., assessment of proximal and distal finger flexion using optical rotary encoders.
2. Vise Grip, e.g., assessment of Jamar grip force using a load cell.
3. Jar/Thermos grip, e.g., assessment of spherical Volar grip torque using a load cell.
4. Coin Pinch, e.g., assessment of pinch force using a load cell.
5. Key lock, e.g., assessment of pinch range of motion and torque using an optical rotary encoder and load cell.
6. Door Handle, e.g., assessment of transverse Volar grip range of motion and torque using an optical rotary encoder and load cell.

For example, the above-listed six example tasks may be measured in at least 22 different ways on both right and left hands for longitudinal assessment of hand function. Each task can be implemented by a corresponding measurement apparatus which can be included in a hand function diagnostic and therapeutic system in a modular fashion. For example, a first application of a system may comprise a first set of tasks and may include the corresponding instrumentation whereas a second application of the system may comprise a second, different set of tasks and corresponding instrumentation.

Each measurement apparatus included in the system may include various sensors, e.g., isometric transducers, used to measure and digitally record hand function responses while a user performs the various tasks. For example, the strength generated by the isometric transducers may be measured and recorded digitally with electronic transmission to a main electronic board for data capture, storage and readout. A graphical user interface, e.g., an LCD display, is provided to provide instructions and visualizations of the test assessments.

Embodiments described herein may be used to ensure care anywhere, care customization, and heath information exchange. As a non-limiting example, a diagnostic module may include six types of testing devices (Composite Finger Flexion, Vise Grip, Jar, Coin, Key and Door Handle) intended to perform 22 measurements on both right and left hands. Such a system may include integrating motor, sensorial, vascular function data. This hospital-based module may serve as the initial step for assessment of the upper extremity functional unit. An application programming interfaces (API) may be developed for Electronic Medical Records that will allow clinicians to place an order and visualize test results at the point of care. In such an approach, healthcare institutions can realize increased efficiency and direct cost savings with automated data capture, and integration, which eliminate human errors and paper transcriptions while facilitating a comprehensive assessment in a single place.

As another non-limiting example, a therapeutic module may be used to facilitate remote rehabilitation. Partial shift of healthcare to the patient's home is an emerging trend in the healthcare business. While this is good for cost containment, it is also good for prompt recovery and better health. The therapeutic module is intended to facilitate remote rehabilitation. Surgical procedures and pharmacological agents' effectiveness can be evaluated through continuous data collection from patient homes. Mobile applications for medication adherence and self-reports augmented by the hand function sensors will be central to the in-home data collection ecosystems. In-hospital skilled nursing care for simple daily activities or hand rehabilitation can be reduced by the capabilities of remote monitors and rehabilitation subsystems. Plans for care customization to individual clinical needs and preferences may be devised from the prescribed grip tools, and self-reports, and others.

As still another non-limiting example, a data analytics and visualization module may be implemented to serve as a data integration hub for Health Information Exchange, and a platform for patient population data visualization and analytics. Predictive models and adaptive clinical decision support models may be developed from this end.

In embodiments, a hand function diagnostic and therapeutic system for automated quantitative assessment of hand function based on a combination of strength, range of motion, and time performance metrics may comprise one or more of the measurement apparatuses described herein. For example, hand function diagnostic and therapeutic system may include one or more of a vise grip measurement apparatus, a thermos grip measurement apparatus, a key lock measurement apparatus, a door handle measurement apparatus, a coin pinch measurement apparatus, proximal finger flexion measurement apparatuses (right and/or left handed), and distal finger flexion measurement apparatuses (right and/or left handed).

In embodiments, the hand function diagnostic and therapeutic system may further include a controller configured to receive measurements from sensors included in the one or more apparatuses, process the received sensor data, and output the processed sensor data. The controller may comprise any suitable computing device comprising one or more processors, e.g., the computing device 1000 described below. In some embodiments, the sensors included in the hand function diagnostic and therapeutic system may comprise digital transducers. In some embodiments, the hand function diagnostic and therapeutic system may further include a display device, e.g., an LCD display device, configured to display instructions and visualizations of test assessments generated from the processed sensor data.

Embodiments disclose herein provide more practical version of the Sollerman Test in terms of time of administration and measurable tasks by capturing hand function signals (e.g., exerted force, finger range of motion, and time to completion of tasks) when various hand grips or functions are performed by a user. Examples, of hand functions which may be tracked by the hand function diagnostic and therapeutic system disclosed herein include: key pinch, transverse/volar grip, Jamar grip, spherical volar grip, and composite finger flexion.

The hand function diagnostic and therapeutic system may comprise a body, e.g., a square or rectangular box-shaped body. The body may further include various doors and compartments containing various measurement apparatuses disclosed herein. For example, the body may contain one or more of a sensorized vise grip (simulating a Jamar dynamometer), a sensorized ball with creases and imprints (simulating a sponge), a sensorized thermos lid with imprints (simulating a jar lid).

The system may additionally provide instructions or guidance, e.g., via a display and/or speaker system, to guide a user in performing various hand functions. As an example, a user's first task may include opening the body, e.g., opening a door of the body if included. The user may then complete various tasks included in the body. The testing duration may be set to a predetermined maximum amount of time, e.g., 10 minutes maximum. The tasks may comprise a series of dependent and continuous steps. For example, starting from the opening of the body, and finishing with its closure. In some examples, a test administrator may monitor performance of the various tasks by a user and may provide additional instructions or guidance to the user. For example, a test administrator may stop a subject's signal recording, should s/he need to complete a task for a subject in order to move to another one.

In some non-limiting embodiments, the body may include a door having a handle type lock that opens with a key. Once the door is open, a user may access a vise grip to squeeze. Squeezing the vise grip may cause a shelf in the box to bring the inside testing materials forward so that they are accessible to the user. For example, the shelf may comprise a platform for the thermos measurement apparatus that the subject will have to open. A sponge with imprints may also sit on the shelf. As a subject squeezes the sponge, s/he may cause the thermos to rise up. After opening the thermos, s/he can also cause the body to close by putting the lid back on the thermos and closing it. The imprints on the surfaces of some testing materials may represent markings of their sensors' positions. The base of the body may be heavy so it doesn't turn upside down during testing. In some embodiments, users may be observed while they are performing the tasks, after some brief instructions. Non-limiting example instructions that may be provided to a user are as follows:

Instructions:

Remember to put each testing material back to its original place before moving to the following task 1. Turn the key to unlock the task box (example: right hand)
2. Turn handle to open the task box
3. Take the vise grip behind the door, and press it to bring the shelf forward
4. Place your fingers on the imprints in the creases of the sponge on the shelf, then squeeze the sponge in your hand to raise the thermos.
5. Open the thermos and close it, to return the shelf to its initial position.
6. Repeat the same sequence for the other hand (example: left hand).

The following Functional Assessment Summary Table shows example tasks which may be provided to a user during operation of a hand function apparatus in accordance with the disclosure:

| Functional Assessment Summary Table | |
|---|---|
| TASKS TO PERFORM | TYPES OF GRIPS |
| 1. Turn key to unlock | Key pinch (sensorized key) |
| 2. Turn handle | Transverse/volar grip (sensorized handle) |
| 3. Squeeze vise grip -- >brings shelf forward | Standard Jamar grip (sensorized vise grip) |
| 4. Squeeze sponge ------- > to raise thermos | Composite finger flexion/ hook grip (sensorized sponge) |
| 5. Open thermos | Spherical volar grip (sensorized) |
| 6. Close thermos----> to return shelf to original position | Spherical volar grip (sensorized) |

Figure 1:
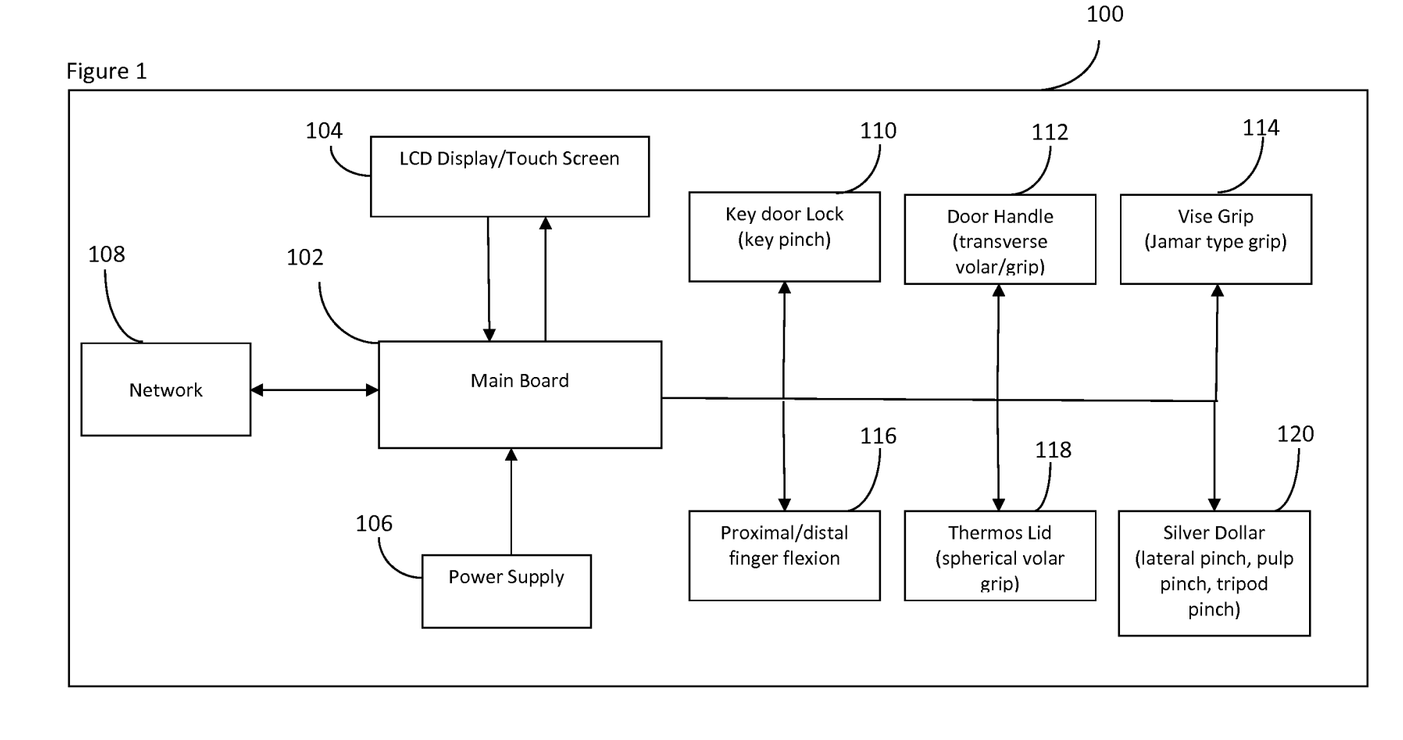
FIG. 1 is a schematic of the hand function diagnostic and therapeutic system described herein.

An example top level block diagram of a hand function diagnostic and therapeutic system 100 is shown in FIG. 1. The main board 102 may comprise a computing device (shown in detail in FIG. 6) configured to implement the central control function. For example, the main board can implement the test executive, interface the subject to the instrumentation, and manage data record storage and retrieval via a suitable connection or network 108, e.g., wireless receiver, USB or Bluetooth. The user may be guided through the various tests using visual (via a display system) and audio (via speakers) instruction. A display device 104, e.g., a color LCD touch screen, can be included to interface the subject to the test executive. The example networks (such as USB and Bluetooth modules) 108 shown in the Figures can interface the test executive to a remote computing device, e.g., a laptop PC, for access to mass storage. A local memory device, e.g., a local flash memory device, can provide protection against data loss in the event of a connection failure, for example. The interface to any or all of the instrumentation can be any appropriate interface, such as an I2C connection. The key lock instrumentation 110 can assess key pinch range of motion and torque using an optical rotary encoder and load cell, for example. In some embodiments, a suitable processor, e.g., a microchip PIC, may converts the signals from the rotary encoder and load cell to angle and torque and transfer the data to the main board via the I2C connection. The door handle instrumentation 112 can be used to assess a transverse Volar grip range of motion and torque using an optical rotary encoder and load cell, for example. A suitable processor, e.g., a microchip PIC, can convert the signals from the rotary encoder and load cell to angle and torque and transfer the data to the main board via the I2C connection. The proximal and distal finger flexion 116 instrumentation can assess composite finger flexion range of motion using an optical rotary encoder. A suitable processor, e.g., a microchip PIC, can convert the signals from the rotary encoder to angle and transfer the data to the main board 102 via any suitable interface such as an I2C. The vise grip instrumentation 114 can assess Jamar grip force using a load cell. A suitable processor, e.g., a microchip PIC, may convert the signals from the rotary encoder and load cell to angle and torque and transfer the data to the main board via an appropriate interface such as an I2C. The thermos instrumentation 118 can assess spherical Volar grip torque using a load cell. A suitable processor, e.g., a microchip PIC, can convert the signals from the load cell to torque and transfer the data to the main board 102 via any suitable interface such as an I2C. The coin pinch instrumentation may assess pinch force using a load cell. A suitable processor, e.g., a microchip PIC, may convert the signals from the load cell to force and transfer the data to the main board 102 via any suitable interface such as an I2C.

The following table summarizes example parameters that an example hand function diagnostic and therapeutic system may target in accordance with various embodiments.

TABLE

| Example targeted parameters | |
| --- | --- |
| No. | Parameters |
| 1. | The following grips may be exercised:<br>Key pinch<br>Transverse/volar grip<br>Jamar-type grip<br>Composite finger flexion<br>Spherical volar grip |
| 2. | The quantities measured during each grip may include:<br>Force/pressure/torque<br>Range of motion<br>Time to complete |
| 3. | The grip exercise devices may simulate the following common household items:<br>Key/door lock (key pinch)<br>Door handle (transverse/volar grip)<br>Vise grip (Jamar-type grip)<br>Sponge/ball (composite finger flexion)<br>Thermos lid (spherical volar grip) |
| 4. | The subject may execute the following sequence of tasks:<br>Turn key to unlock door<br>Rotate handle to open door<br>Pickup vise grip from base or mount and squeeze to expose sponge<br>Return vise grip to base or mount<br>Pickup sponge from base or mount and squeeze to expose thermos<br>Return sponge to base or mount<br>Rotate and remove thermos lid to receive treat<br>Replace thermos lid and close up task box |
| 5. | Each task may be repeated thrice. The highest force exerted by the subject may be retained. |
| 6. | On completion of one task, the subject's attention may be drawn to the next task to make the procedure intuitive. |
| 7. | The administrator may have the ability to override the process stopping a task at any point and proceeding to the next task. |
| 8. | The grip exercise devices may have imprints indicating the correct placement of digits. |
| 9. | The sponge/ball and vise grip may be free to move about limited only by a communication cable. |
| 10. | The test materials may be robust. |
| 11. | The system may be scalable. |
| 12. | The system may be easy and fun to use. |

The following tables show example non-limiting engineering parameters of an example hand function diagnostic and therapeutic system may target in accordance with various embodiments. In the following tables, each engineering parameter is cross referenced to the customer parameter (shown in the table above) from which it was derived.

| Functionality and Performance | | | |
| --- | --- | --- | --- |
| No. | Customer Parameter | Engineering Parameter | Justification |
| 1. | 1, 2, 3 | A simulated key lock instrumented with torque and angular displacement sensors may be mounted in or near the front door. | Simulates an activity of daily life. |
| 2. | 6, 12 | A light mounted near the key lock may illuminate when the test is active. | Prompts the subject to begin the task. |
| 3. | 5, 10 | Three attempts at turning the key clockwise may be recorded. | The highest force exerted by the subject may be retained. |

-continued

| | | Functionality and Performance | |
|---|---|---|---|
| No. | Customer Parameter | Engineering Parameter | Justification |
| 4. | 4, 6, 12 | After the third attempt, the key lock test indicator may turn off and the door handle test indicator may illuminate. | Prompts the subject to begin the next task. |
| 5. | 1, 2, 3 | A simulated door handle instrumented with torque and angular displacement sensors may be mounted in or near the front door. | Simulates an activity of daily life. |
| 6. | 6, 12 | A light mounted near the door handle may illuminate when the test is active. | Prompts the subject to begin the task. |
| 7. | 5, 10 | Three attempts at turning the door handle clockwise may be recorded. | The highest force exerted by the subject is retained. |
| 8. | 4, 6, 12 | After the third attempt, the door handle test indicator may turn off and the door may open exposing a vise grip. | Prompts the subject to begin the next task. |
| 9. | 1, 2, 3 | A vise grip instrumented with force and displacement sensors may rest on a base inside of the front door. | Simulates an activity of daily life. |
| 10. | 6, 12 | A light mounted near the vise grip may illuminate indicating that the test is active. An indication of exerted force may be displayed on a display device | Prompts the subject to begin the task. |
| 11. | 5, 10 | Three attempts at squeezing the vise grip may be recorded. | The highest force exerted by the subject may be retained. |
| 12. | 4, 6, 12 | After the third attempt, the vise grip light may turn off and a compartment containing the sponge/ball grip may open. | Prompts the subject to begin the next task. |
| 13. | 1, 2, 3 | A sponge/ball grip instrumented with pressure sensors may rest in a closable compartment. | Simulates an activity of daily life. |
| 14. | 6, 12 | A light mounted in the compartment may illuminate when the test is active. | Prompts the subject to begin the task. |
| 15. | 5, 10 | Three attempts at squeezing the sponge/ball grip may be recorded. | Allows exclusion of outliers. |
| 16. | 4, 6, 12 | After the third attempt, the sponge/ball grip light may turn off and a compartment containing the thermos may open. | Prompts the subject to begin the next task. |
| 17. | 1, 2, 3 | A thermos instrumented with torque and angular displacement sensors may be fixed to the bottom of a closable compartment with access from the top and sides. In some embodiments, markings may be included for the closing position and the opening direction (e.g., clockwise) | Simulates an activity of daily life. |
| 18. | 6, 12 | A light mounted in the compartment may illuminate when the test is active. | Prompts the subject to begin the task. |
| 19. | 5, 10 | Three attempts at opening the thermos lid may be recorded. | Allows exclusion of outliers. |
| 20. | 4, 6, 12 | After the third attempt, the thermos light may turn off, and the thermos may open revealing a treat or displaying a positive indication. | Rewards subject for completing the task. E.g., "Well done!" |
| 21. | 5, 10 | An attempt may be counted when interval of increasing force or displacement is followed by an interval of zero or decreasing force or displacement. | Allows all three quantities specified in customer requirement (2) to be recorded. |
| 22. | 12 | An indicator similar to a bar graph or tachometer may provide visual and aural feedback on progress with each attempt. | Reassures the subject that they are executing the test correctly. |

Functionality and Performance

| No. | Customer Parameter | Engineering Parameter | Justification |
|---|---|---|---|
| 23. | 12 | The progress indicator may display force, torque, pressure, or displacement graphically. | To indicate progess. |
| 24. | 12 | The progress indicator may include a "high water mark" that resets between tasks. | Encourages the subject to try harder with each attempt. |
| 25. | 11 | Data recorded during an assessment may be transferred to a computer via USB or other standard interface. | Allows post processing and permanent storage. |
| 26. | 11 | Data may be stored in text format with a structure that can be easily parsed. | Simplifies retrieval and post processing. |
| 27. | 11 | System components (i.e. sensors) may use a standard interface and communication protocol. | Enhances scalability and reuse. |
| 28. | 11 | System control components may be implemented in standard programmable devices (i.e. micro-controllers, FPGAs) | Enhances scalability and reuse. Allows customization. |
| 29. | 7 | An administrator override function may be provided to stop an active task and proceed to the next. | Handles the case of a subject who is unable to complete a task. |
| 30. | 7 | A reset function may be provided to immediately end testing. | Handles the case of a subject who is unable continue the assessment. |
| 31. | 8 | The grip exercise devices may have imprints indicating the correct placement of digits when necessary. | |
| 32. | 9 | The sponge/ball and vise grip may be free to move about limited only by a communication cable. | |
| 33. | 9 | Key, door handle, and thermos tasks may be annotated with opening and closing directions (CW or CCW). | |

Operational (Physical) Environment

| Customer Parameter | Engineering Parameter | Justification |
|---|---|---|
| 12 | The system may be powered by a standard 110 V AC wall receptacle and draw less than 10 A. | Eases installation and enhances portability. |
| 12 | The system may operate in an ambient temperature range of 20-30° C. | The expected test environment is room temperature. |
| 12 | The system may not be waterproof. | Sealing moving parts would come at a high cost. The expected test environment is dry air. |
| 12 | The system may not require periodic maintenance. | Operational costs should be low. |
| 12 | The system may weigh less than 100 lbs. | Eases installation and enhances portability. |
| 12 | The system may be less than 1 meter in height, width, and depth. | Eases installation and enhances portability. |
| 12 | An automated procedure may be developed that minimizes administrator time and effort if a calibration routine is performed | Operational costs should be low. |

Figure 2:
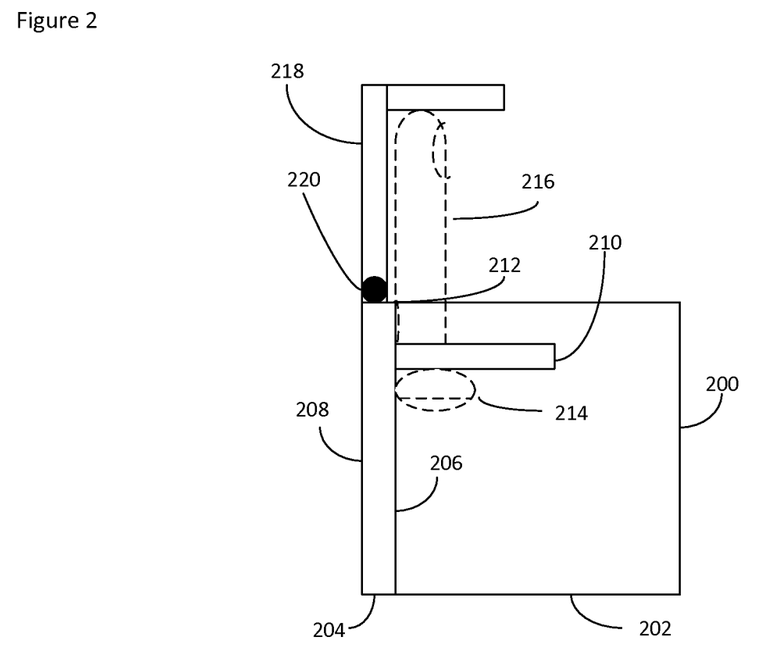
FIG. 2 is a top view of a proximal finger flexion measurement instrument in resting position.
Figure 3:
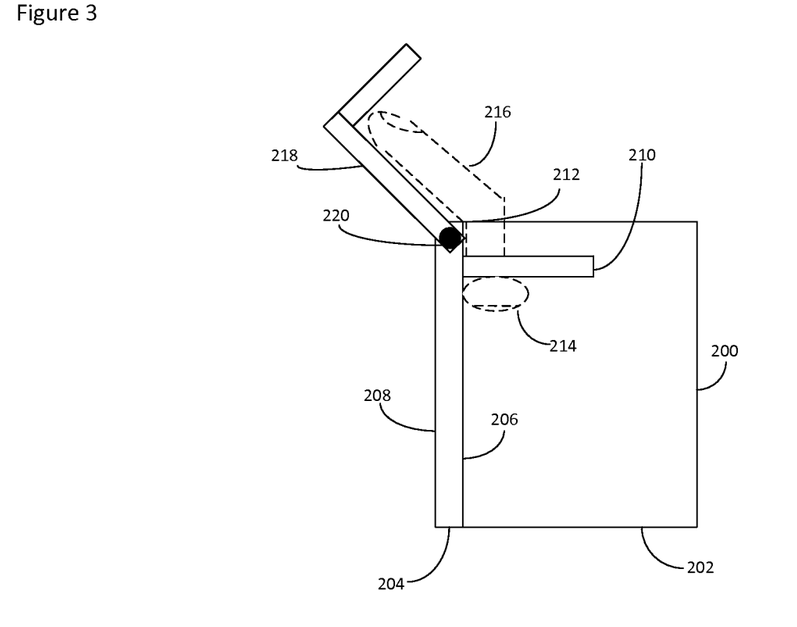
FIG. 3 is a top view of a proximal finger flexion measurement instrument during flexion of the fingers.
Figure 4:
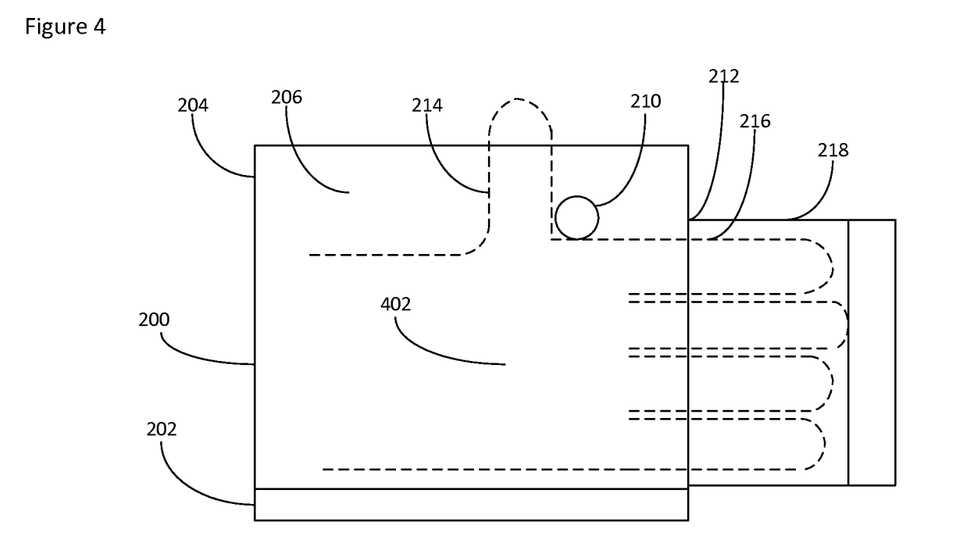
FIG. 4 is a side view of a proximal finger flexion measurement instrument.

An example of a proximal finger flexion measurement apparatus 200 is shown in FIGS. 2-4. The embodiment shown in FIGS. 2-4 is configured for use with the right hand. One of skill in the art in light of this disclosure can create such an apparatus for the left hand without undue experimentation. The apparatus shown in FIGS. 2-4 comprises a base platform 202 and a palm platform 204 perpendicularly coupled to the base platform 202. The palm platform 204 has opposing first 206 and second 208 surfaces. The first 206 and second 208 surfaces are substantially perpendicular to the base platform 202. The proximal finger flexion measurement apparatus 200 further comprises a hand positioning member 210 perpendicularly coupled to the first surface 206 of the palm platform 202 and extending a distance away from the first surface of the palm platform. In some embodiments, the hand positioning member 210 can be cylindrical. Additionally, in some examples, the hand positioning member 210 can extend at least 1 cm away from the first surface 206 of the palm platform 204.

The hand positioning member 210 can be coupled to the first surface 206 of the palm platform 204 adjacent to an edge 212 of the palm platform at a location such that when a user positions a palm of the hand 402 (in FIG. 4) on the first surface 206 of the palm platform 204 with the hand positioning member 210 touching the base of the thumb 214 of the hand 402 between thumb 214 and index finger 216 of the hand, the edge of the palm platform is located beneath the knuckles of the hand 402 thereby permitting the user to pivot the fingers 216 about the knuckles while the palm rests on the first surface 206 of the palm platform 204. The proximal finger flexion surface 218 can be rotatably coupled via a pivoting member 220 to and perpendicular with the base platform 202 at a location adjacent to the edge of the palm platform 204 such that the proximal finger flexion surface 218 extends away from the second surface of the palm platform 204, such that when a user positions the palm of the hand 402 on the first surface 206 of the palm platform 204 with the hand positioning member 210 touching the base of the thumb 214 of the hand 402 between thumb 214 and index finger 216 of the hand, at least a portion of the fingers 216 of the hand 402 interface with the proximal finger flexion surface 218. The proximal finger flexion surface 218 can be biased to remain in a resting position relative to the palm platform 204. In the resting position the proximal finger flexion surface 218 forms an angle with the first surface of the palm platform (as shown in FIG. 2). For example, the angle may be substantially equal to or less than 90 degrees.

When the user applies a force to the proximal finger flexion surface 218 via the fingers 216 (illustrated in FIG. 3), the proximal finger flexion surface 218 is rotated toward the second surface of the palm platform 208 such that the angle between the proximal finger flexion surface 218 and the first surface 206 of the palm platform 204 increases and rotates a sensor, e.g., an optical rotary sensor, in communication with the pivoting member 220. Although the proximal finger flexion surface 218 is shown in the Figures as covering the fingers 216, the proximal finger flexion surface 218 can also be flat, can angle away from the fingers, or can contain depressions to cradle the fingers.

Figure 5:
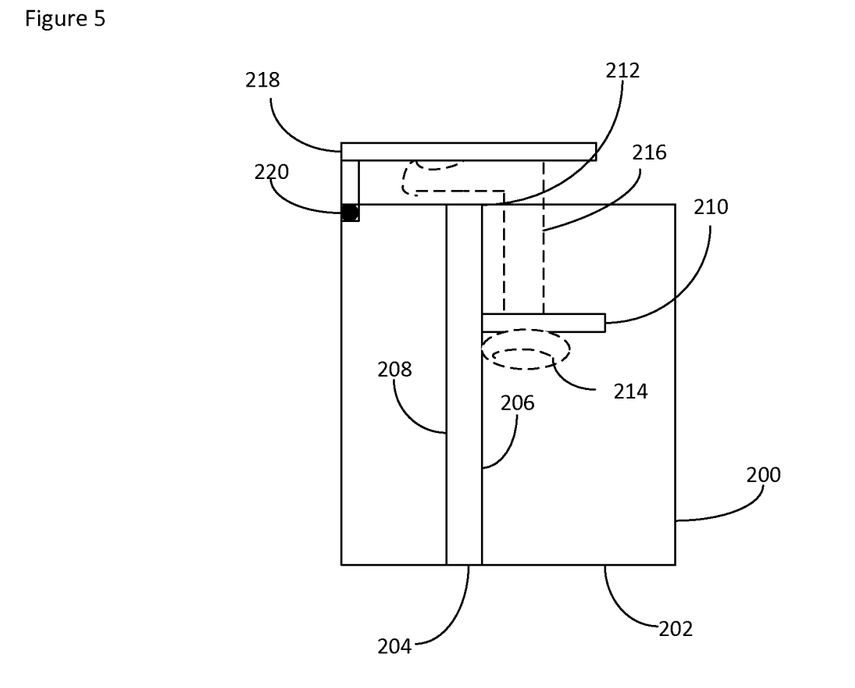
FIG. 5 is a top view of a distal finger flexion measurement instrument in resting position.
Figure 6:
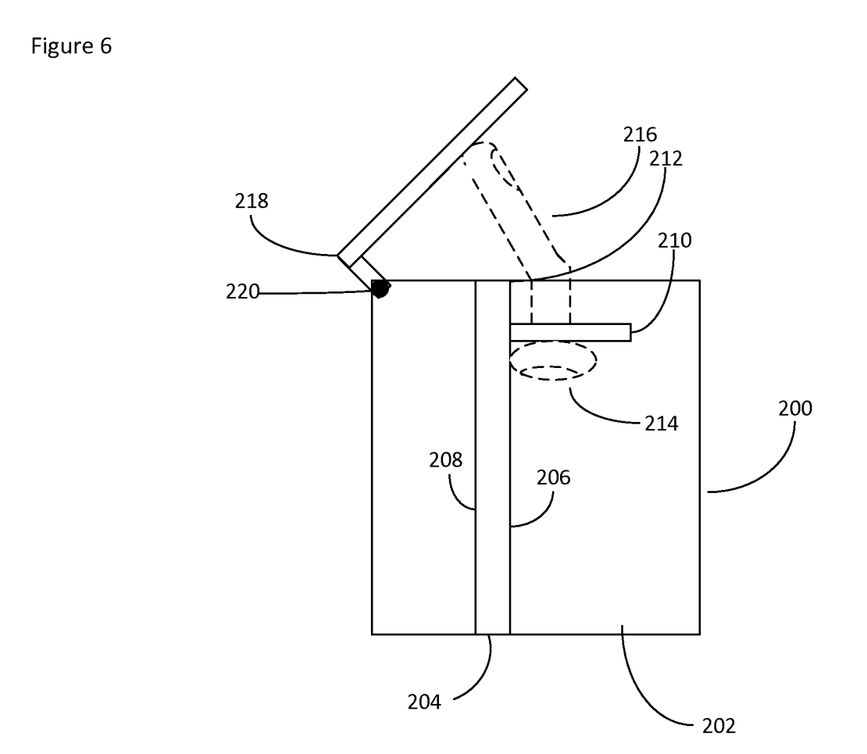
FIG. 6 is a top view of a distal finger flexion measurement instrument during flexion of the fingers.
Figure 7:
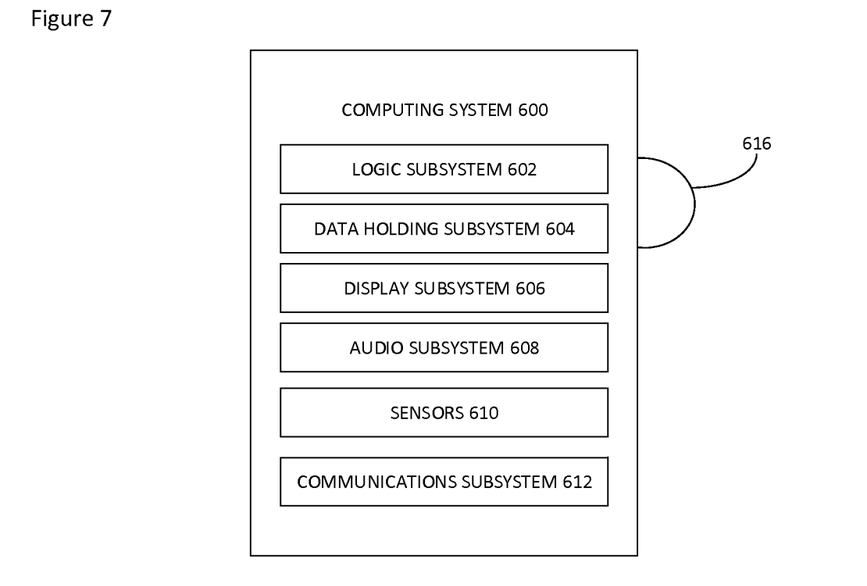
FIG. 7 is a diagram depicting a computing system.

A distal finger flexion version of the apparatus is shown in FIGS. 5-6. The embodiment shown in FIGS. 5-6 is configured for use with the right hand. One of skill in the art in light of this disclosure can create such an apparatus for the left hand without undue experimentation. As shown in FIGS. 5 and 6, a distal finger flexion version of the disclosed apparatus can comprise a base platform 202 and a palm platform 204 perpendicularly coupled to the base platform 202. The palm platform 204 has opposing first 206 and second 208 surfaces where the first 206 and second 208 surfaces are substantially perpendicular to the base platform 202. The distal finger flexion version of the apparatus 200 also includes a hand positioning member 210 perpendicularly coupled to the first surface 206 of the palm platform 204 and extending a distance away from the first surface 206 of the palm platform 204. In some examples, the hand positioning member 210 can be cylindrical and can extend at least 1 cm away from the first surface 206 of the palm platform 204. The hand positioning member 210 is coupled to the first surface 206 of the palm platform 204 at a distance from an edge of the palm platform such that when a user positions the palm of the hand 402 on the first surface 206 of the palm platform 204 with the hand positioning member 210 touching the base of the thumb 214 of the hand 402 between the thumb 214 and index finger 216 of the hand 402, the edge 212 of the palm platform 204 is located beneath the proximal phalanges the hand 402 thereby permitting the user to pivot the distal ends of the fingers 216 while the palm rests on the first surface 206 of the palm platform 204. The distal finger flexion version further comprises a distal finger flexion surface 218 rotatably coupled via a pivoting member 220 to and perpendicular with the base platform 200 at a location adjacent to the edge 212 of the palm platform 204 such that the distal finger flexion surface 218 extends away from the second surface 208 of the palm platform 204. When a user positions the palm of the hand 402 on the first surface 206 of the palm platform 208 with the hand positioning member 210 touching the base of the thumb 214 of the hand 402 between the thumb 214 and index finger 216 of the hand 402, the distal ends of the fingers 216 of the hand 402 interface with the distal finger flexion surface 218. The distal finger flexion surface is biased to remain in a resting position relative to the palm platform (as shown in FIG. 5), wherein in the resting position the distal finger flexion surface 218 forms an angle with the first surface 206 of the palm platform 204. In embodiments, the angle may be substantially equal to or less than 90 degrees. When the user applies a force to the distal finger flexion surface 218 via the fingers (as illustrated in FIG. 6), the distal finger flexion surface 218 is rotated toward the second surface 208 of the palm platform 204 such that the angle between the distal finger flexion surface 218 and the first surface 206 of the palm platform 218 increases and rotates a sensor, e.g., an optical rotary sensor, in communication with the pivoting member 218.

For any of the above devices, any one, two, three, or all four fingers can be exercised depending upon the placement of the proximal or distal finger flexion surface relative to the hand positioning member.

The following shows example data that can be output by a hand function diagnostic and therapeutic system in accordance with the disclosure following a completion by a user of a series of hand function tests.

| Left Key Force | Left Proximal Finger Flexion | Left Pulp Pinch |
|---|---|---|
| Trial #1: 0 lb 0 s | Trial #1: 0 deg 0 s | Trial #1: 0 lb 0 s |
| Trial #2: 0 lb 0 s | Trial #2: 0 deg 0 s | Trial #2: 0 lb 0 s |
| Trial #3: 0 lb 0 s | Trial #3: 0 deg 0 s | Trial #3: 0 lb 0 s |
| Right Key Force | Right Proximal Finger Flexion | Right Pulp Pinch |
| Trial #1: 0 lb 0 s | Trial #1: 44800 deg 2 s | Trial #1: 0 lb 0 s |
| Trial #2: 0 lb 0 s | Trial #2: 35584 deg 4 s | Trial #2: 0 lb 0 s |
| Trial #3: 0 lb 0 s | Trial #3: 56577 deg 5 s | Trial #3: 0 lb 0 s |
| Left Key Angle | Left Distal Finger Flexion | Left Lateral Pinch |
| Trial #1: 0 deg 0 s | Trial #1: 0 deg 0 s | Trial #1: 0 lb 0 s |
| Trial #2: 0 deg 0 s | Trial #2: 0 deg 0 s | Trial #2: 0 lb 0 s |
| Trial #3: 0 deg 0 s | Trial #3: 0 deg 0 s | Trial #3: 0 lb 0 s |
| Right Key Angle | Right Distal Finger Flexion | Right Lateral Pinch |
| Trial #1: 0 deg 0 s | Trial #1: 0 deg 0 s | Trial #1: 0 lb 0 s |
| Trial #2: 0 deg 0 s | Trial #2: 0 deg 0 s | Trial #2: 0 lb 0 s |
| Trial #3: 0 deg 0 s | Trial #3: 0 deg 0 s | Trial #3: 0 lb 0 s |
| Left Door Force | Left Vise Grip | Left Tripod Pinch |
| Trial #1: 0 lb 0 s | Trial #1: 0 lb 0 s | Trial #1: 0 lb 0 s |
| Trial #2: 0 lb 0 s | Trial #2: 0 lb 0 s | Trial #2: 0 lb 0 s |
| Trial #3: 0 lb 0 s | Trial #3: 0 lb 0 s | Trial #3: 0 lb 0 s |
| Right Door Force | Right Vise Grip | Right Tripod Pinch |
| Trial #1: 0 lb 0 s | Trial #1: 0 lb 0 s | Trial #1: 0 lb 0 s |
| Trial #2: 0 lb 0 s | Trial #2: 0 lb 0 s | Trial #2: 0 lb 0 s |
| Trial #3: 0 lb 0 s | Trial #3: 0 lb 0 s | Trial #3: 0 lb 0 s |
| Left Door Angle | Left Thermos Grip | |
| Trial #1: 0 deg 0 s | Trial #1: 0 lb 0 s | |
| Trial #2: 0 deg 0 s | Trial #2: 0 lb 0 s | |
| Trial #3: 0 deg 0 s | Trial #3: 0 lb 0 s | |
| Right Door Angle | Right Thermos Grip | |
| Trial #1: 0 deg 0 s | Trial #1: 0 lb 0 s | |
| Trial #2: 0 deg 0 s | Trial #2: 0 lb 0 s | |
| Trial #3: 0 deg 0 s | Trial #3: 0 lb 0 s | |

In some embodiments, a computing system including one or more processors may be included in the systems and/or apparatuses described herein. Additionally, in embodiments the above described methods and processes may be tied to a computing system, including one or more computers. In particular, the methods and processes described herein may be implemented as a computer application, computer service, computer API, computer library, and/or other computer program product.

FIG. 6 schematically shows a non-limiting computing device 600 that can perform one or more of the above described methods and processes and can be included in various systems and/or apparatuses disclosed herein. Computing device 600 is shown in simplified form. It is to be understood that virtually any computer architecture can be used without departing from the scope of this disclosure. In different embodiments, the computing device 600 can take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 600 includes a logic subsystem 602 and a data-holding subsystem 604. Computing device 600 may also include a display subsystem 606, an audio subsystem 608, one or more capture devices 610, a communication subsystem 612, and/or other components not shown in FIG. 6. Computing device 600 can also optionally include user input devices such as manually actuated buttons, switches, keyboards, mice, game controllers, cameras, microphones, and/or touch screens, for example.

Logic subsystem 602 can include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 604 can include one or more physical, non-transitory, devices configured to hold data and/or instructions executable by the logic subsystem to implement the herein described methods and processes. When such methods and processes are implemented, the state of data-holding subsystem 604 can be transformed (e.g., to hold different data).

Data-holding subsystem 604 can include removable media and/or built-in devices. Data-holding subsystem 604 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 604 can include devices with one or more of the following characteristics: volatile, nonvolatile, dynamic, static, read/write, read-only, random access, sequential access, location addressable, file addressable, and content addressable. In some embodiments, logic subsystem 602 and data-holding subsystem 604 can be integrated into one or more common devices, such as an application specific integrated circuit or a system on a chip.

FIG. 6 also shows an aspect of the data-holding subsystem in the form of removable computer-readable storage media 616, which can be used to store and/or transfer data and/or instructions executable to implement the herein described methods and processes. Removable computer-readable storage media 616 can take the form of CDs, DVDs, HD-DVDs, Blu-Ray Discs, EEPROMs, flash memory cards, and/or floppy disks, among others.

When included, display subsystem 606 can be used to present a visual representation of data held by data-holding subsystem 604. As the herein described methods and processes change the data held by the data-holding subsystem, and thus transform the state of the data-holding subsystem, the state of display subsystem 606 may likewise be transformed to visually represent changes in the underlying data. Display subsystem 606 may include one or more display devices or surfaces utilizing virtually any type of technology. Such display devices or surfaces may be combined with logic subsystem 602 and/or data-holding subsystem 604 in a shared enclosure, or such display devices or surfaces may be peripheral display devices or surfaces.

When included, audio subsystem 608 can be used to present an audio representation of data held by data-holding subsystem 604. As the herein described methods and processes change the data held by the data-holding subsystem, and thus transform the state of the data-holding subsystem, the state of audio subsystem 608 may likewise be transformed to represent changes in the underlying data via sounds or vibrations. Audio subsystem 608 may include one or more devices or components capable of vibration, e.g., speakers or the like. Such devices may be combined with logic subsystem 602 and/or data-holding subsystem 604 in a shared enclosure, or such devices may be peripheral devices. In some embodiments, computing device 600 can additionally include a haptic subsystem including one or vibration components which can be used to present haptic representations of data held by data-holding subsystem 604.

Computing system 600 may further include one or more sensors 610 configured to obtain various measurements. Examples of sensors which may be included in computing system 600 are described herein, e.g., optical rotary sensors, etc.

When included, communication subsystem 612 can be configured to communicatively couple computing device 600 with one or more other computing devices and/or with various external sensors, components, or systems. Communication subsystem 612 can include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing system 600 to send and/or receive messages to and/or from other devices via a network such as the Internet.

Computing system 600 can further include various subsystems configured to execute one or more instructions that are part of one or more programs, routines, objects, components, data structures, or other logical constructs. Such subsystems may be operatively connected to logic subsystem 602 and/or data-holding subsystem 604. In some examples, such subsystems can be implemented as software stored on a removable or non-removable computer-readable storage medium.

It is to be understood that the embodiments described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various apparatuses, processes, systems and configurations, and other features, functions, acts, and/or properties disclosed herein, as well as any and all equivalents thereof.

The invention claimed is:

1. A proximal finger flexion measurement apparatus, comprising:
    a base platform;
    a palm platform perpendicularly coupled to the base platform, the palm platform having opposing first and second surfaces where the first and second surfaces are substantially perpendicular to the base platform;
    a hand positioning member perpendicularly coupled to the first surface of the palm platform, and extending a distance away from the first surface of the palm platform,
    wherein the hand positioning member is coupled to the first surface of the palm platform at a location above the base platform sufficient to allow a user to position a hand between the hand positioning member and the base platform with the palm of the hand in contact with the first surface and adjacent to an edge of the palm platform at a location such that when a user positions the palm of a hand on the first surface of the palm platform with the hand positioning member touching a base of a thumb of the hand between the thumb and an index finger of the hand, the edge of the palm platform is located beneath at least one knuckle of the hand, thereby permitting the user to pivot at least one finger about the at least one knuckle while the palm rests on the first surface of the palm platform;
    a proximal finger flexion surface rotatably coupled via a pivoting member to and perpendicular with the base platform at a location adjacent to the edge of the palm platform such that the proximal finger flexion surface extends away from the second surface of the palm platform, such that when a user positions the palm of the hand on the first surface of the palm platform with the hand positioning member touching the base of the thumb of the hand between thumb and index finger of the hand, at least one finger of the hand interfaces with the proximal finger flexion surface, and
    where the proximal finger flexion surface is biased to remain in a resting position relative to the palm platform, wherein in the resting position the proximal finger flexion surface forms an angle with the first surface of the palm platform, wherein the angle is substantially equal to or less than 90 degrees, and when the user applies a force to the proximal finger flexion surface via the at least one finger, the proximal finger flexion surface is rotated toward the second surface of the palm platform such that the change in angle between the proximal finger flexion surface and the first surface of the palm platform increases and is measured by an angular displacement sensor in communication with the pivoting member.

2. The apparatus of claim 1, wherein the angular displacement sensor is an optical rotary sensor.

3. The apparatus of claim 1, wherein the hand positioning member is cylindrical.

4. The apparatus of claim 1, wherein the hand positioning member extends at least 1 cm away from the first surface of the palm platform.

5. The apparatus of claim 1, wherein the proximal finger flexion measurement apparatus is configured to measure proximal finger flexion of a left hand of a user and the first surface of the palm platform is a left surface of the palm platform.

6. The apparatus of claim 1, wherein the proximal finger flexion measurement apparatus is configured to measure proximal finger flexion of a right hand of a user and the first surface of the palm platform is a right surface of the palm platform.

7. A distal finger flexion measurement apparatus, comprising:
    a base platform;
    a palm platform perpendicularly coupled to the base platform, the palm platform having opposing first and second surfaces where the first and second surfaces are substantially perpendicular to the base platform;
    a hand positioning member perpendicularly coupled to the first surface of the palm platform and extending a distance away from the first surface of the palm platform,
    wherein the hand positioning member is coupled to the first surface of the palm platform at a location above the base platform sufficient to allow a user to position a hand between the hand positioning member and the base platform with a palm of the hand in contact with the first surface and at a distance from an edge of the palm platform such that when a user positions the palm of a hand on the first surface of the palm platform with the hand positioning member touching a base of a thumb of the hand between the thumb and an index finger of the hand, the edge of the palm platform is located beneath at least one proximal phalanx of the hand thereby permitting the user to pivot the distal ends of the fingers while the palm rests on the first surface of the palm platform;
    a distal finger flexion surface rotatably coupled via a pivoting member to and perpendicular with the base platform at a location adjacent to the edge of the palm platform such that the distal finger flexion surface extends away from the second surface of the palm platform, such that when a user positions the palm of the hand on the first surface of the palm platform with the hand positioning member touching the base of the thumb of the hand between thumb and index finger of the hand, the distal ends of the fingers of the hand interface with the distal finger flexion surface, and
    where the distal finger flexion surface is biased to remain in a resting position relative to the palm platform, wherein in the resting position the distal finger flexion surface forms an angle with the first surface of the palm platform, wherein the angle is substantially equal to or less than 90 degrees, and when the user applies a force to the distal finger flexion surface via the fingers, the distal finger flexion surface is rotated toward the second surface of the palm platform such that the change in angle between the distal finger flexion surface and the first surface of the palm platform increases and is measured by an angular displacement sensor in communication with the pivoting member.

8. The apparatus of claim 7, wherein the angular displacement sensor is an optical rotary sensor.

9. The apparatus of claim 7, wherein the hand positioning member is cylindrical.

10. The apparatus of claim 7, wherein the hand positioning member extends at least 1 cm away from the first surface of the palm platform.

11. The apparatus of claim 7, wherein the distal finger flexion measurement apparatus is configured to measure distal finger flexion of a left hand of a user and the first surface of the palm platform is a left surface of the palm platform.

12. The apparatus of claim 7, wherein the distal finger flexion measurement apparatus is configured to measure distal finger flexion of a right hand of a user and the first surface of the palm platform is a right surface of the palm platform.

13. A hand function diagnostic and therapeutic system for automated quantitative assessment of hand function based on a combination of strength, range of motion, and time to completion, comprising:
   one or more of the measurement apparatuses of claim 1 or claim 7; and
   a controller configured to receive measurements from sensors included in the one or more apparatuses, process the received sensor data, and output the processed sensor data.

14. The system of claim 13, wherein the sensors comprise digital transducers.

15. The system of claim 13, further comprising a display device configured to display instructions and visualizations of test assessments generated from the processed sensor data.

* * * * *